United States Patent
Alfano et al.

(10) Patent No.: US 10,420,471 B2
(45) Date of Patent: Sep. 24, 2019

(54) METHOD OF DEEP TISSUE IMAGING USING MULTI-PHOTON EXCITATION OF A FLUOROPHORE

(71) Applicant: Research Foundation of the City University of New York, New York, NY (US)

(72) Inventors: Robert R. Alfano, Bronx, NY (US); Yang Pu, New York, NY (US); Lingyan Shi, New York, NY (US); Sebastião Pratavieira, São Paulo (BR)

(73) Assignee: Research Foundation of the City University of New York, New York, NY (US)

( * ) Notice: Subject to any disclaimer, the term of this patent is extended or adjusted under 35 U.S.C. 154(b) by 1395 days.

(21) Appl. No.: 14/299,564

(22) Filed: Jun. 9, 2014

(65) Prior Publication Data

US 2014/0371582 A1 Dec. 18, 2014

Related U.S. Application Data

(60) Provisional application No. 61/956,620, filed on Jun. 13, 2013.

(51) Int. Cl.
*A61B 5/00* (2006.01)
*A61N 5/06* (2006.01)
(Continued)

(52) U.S. Cl.
CPC .............. *A61B 5/0071* (2013.01); *A61B 5/00* (2013.01); *A61B 5/0059* (2013.01); *A61N 5/062* (2013.01);
(Continued)

(58) Field of Classification Search
CPC .... A61N 5/062; A61B 5/0071; A61B 5/0059; A61B 5/00; A61B 1/00; A61B 5/0082;
(Continued)

(56) References Cited

U.S. PATENT DOCUMENTS

| | | | |
|---|---|---|---|
| 2008/0233051 A1* | 9/2008 | Prasad | A61K 31/695 424/9.6 |
| 2011/0021970 A1* | 1/2011 | Vo-Dinh | A61K 49/0039 604/20 |
| 2012/0309045 A1* | 12/2012 | Knutson | G01N 21/6428 435/29 |

OTHER PUBLICATIONS

Lihong V. Wang, "Multiscale Photoacoustic Microscopy and Computed Tomography", Nature Photonics, vol. 3, Sep. 2009, Optical Imaging Laboratory, Department of Biomedical Engineering, Washington University in St. Louis, p. 503 (1 pg.).
Anderson, R.R. et al., "The Optics of Human Skin", J. Invest Dermatol. Jul. 1981; 77(1):13-9, 1 page.
(Continued)

*Primary Examiner* — Amanda Lauritzen Moher
(74) *Attorney, Agent, or Firm* — Peter J. Mikesell; Schmeiser, Olsen & Watts, LLP

(57) ABSTRACT

A method is provided for deep tissue imaging using multi-photon excitation of a fluorescent agent. The fluorescent agent is irradiated with an ultrafast laser to produce an excited singlet state ($S_n$) which subsequently undergoes non-radiative relaxation to a first singlet state ($S_1$). The $S_1$ state undergoes fluorescence to the ground state $S_0$ to produce an emission wavelength. Both the excitation and emission wavelengths are within the near infrared optical window, thereby permitting deep tissue penetration for both the incoming and outgoing signals.

22 Claims, 11 Drawing Sheets

(51) Int. Cl.
- *G01N 21/00* (2006.01)
- *G01N 21/64* (2006.01)
- *G01N 21/17* (2006.01)
- *A61B 1/00* (2006.01)
- *G01N 21/62* (2006.01)
- *G01N 21/63* (2006.01)
- *A61K 49/00* (2006.01)

(52) U.S. Cl.
CPC .............. *G01N 21/00* (2013.01); *G01N 21/17* (2013.01); *G01N 21/6486* (2013.01); *A61B 1/00* (2013.01); *A61B 5/0082* (2013.01); *A61K 49/001* (2013.01); *A61K 49/0013* (2013.01); *A61K 49/0019* (2013.01); *A61K 49/0021* (2013.01); *G01N 21/62* (2013.01); *G01N 21/63* (2013.01)

(58) Field of Classification Search
CPC .... G01N 21/17; G01N 21/6486; G01N 21/00; G01N 21/62; G01N 21/63; A61K 49/0013; A61K 49/0021; A61K 49/001; A61K 49/0019
See application file for complete search history.

(56) References Cited

OTHER PUBLICATIONS

Yici Guo et al., "Noninvasive Two-photon-excitation Imaging of Tryptophan Distribution in Highly Scattering Biiological Tissues", Elsevier Science B.V. Copyright 1996, 0030-4018/98/$ (PII: S0030-4018(98)00207-7), Optics Communiations 154 (1998) 383-389 (7 pgs.).

Mikhail Y. Erezin et al., "Two-Photon Optical Properties of Near-Infrared Dyes at 1.55 μm Excitation", The Journal of Physical Chemistry, ACS Publications, copyright 2011 American Chemical Society, dx.doi.org/10.1021/jp207618e. J. Phys. Chem. B 2011, 115, pp. 11530-11535 (total 6 pgs.).

S. Frigerio et al., "Light Conversion in Photosynthetic Organisms", Jan. 2008 (14 pgs.).

Zongren Zhang et al., "Near-Infrared Dichromic Fluorescent Carbocyanine Molecules", Angew. Chem. Int. Ed. 2008, wiley-VCH Verlag GmbH & Co., KGaA, Weinheim, DOI: 10.1002/anie.200800475, pp. 3584-3587 (4 pgs.).

Emmanuelle Chaigneau, Impact of Wavefront Distortion and Scattering on 2-Photon Microscopy in Mammalian Brain Tissue, Optics Express 22755, vol. 19, No. 23, Nov. 7, 2011 #153135- $15.00 USD, (20 pgs.).

* cited by examiner

| FLUORESCENT AGENTS | SOLVENT | $S_2$ OR $S_n$ (nm) | $S_1$ (nm) | EMISSION PEAK (nm) |
|---|---|---|---|---|
| Chl a | Ethyl | 404 | 629 | 680 |
| ICG* | DMSO | 398 | 779 | 695, 820 |
| Diprotonated-tetraphenylporphyrin | Chloroform+HCl | 446 | 662 | 687 |
| MgOEP | Toluene | 410 | 582 | 638 |
| N-Confused tetraphenylporphyrin | Chloroform | 439 | 730 | 750 |
| Octaethylporphyrin | Benzene | 402 | 621 | 689 |
| Pheophorbide a | Ethanol | 410 | 669 | 674 |
| Porphin | Toluene | 396 | 566 | 684 |
| Pyropheophorbide a methyl ester | Dichloromethane | 413 | 666 | 674 |
| Pyropheophorbide a | Dichloromethane | 412 | 668 | 675 |
| TBP-beta-octa(COOBu)-Fb | DMF | 433 | 675 | 750 |
| TBP-beta-octa(COOBu)-Zn | DMF | 453 | 644 | 709 |
| TBP-meso-tetra(4-COOMe-phenyl)-Fb | DMF | 469 | 642 | 807 |
| TBP-meso-tetra(4-COOMe-phenyl)-Zn | DMF | 469 | 659 | 741 |
| Tetrakis (2,6-dichlorophenyl) porphyrin | Toluene | 418 | 592 | 717 |
| Tetrakis (o-aminophenyl) porphyrin | Toluene | 406 | 633 | 717 |
| Tetramesitylporphyrin, (TMP) | Toluene | 426 | 603 | 721 |

* ICG was selected as an example from the family of Cyanine and its derivative dyes which have similar spectral characteristics.

FIG. 4

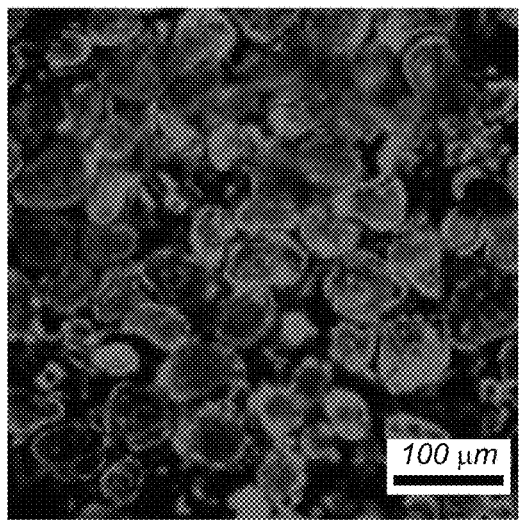
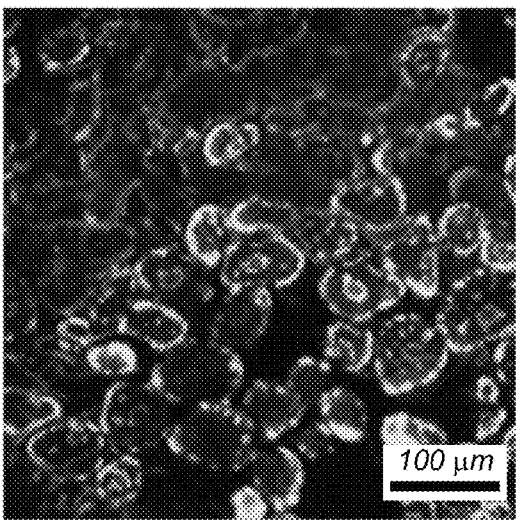
FIG. 7A  FIG. 7B
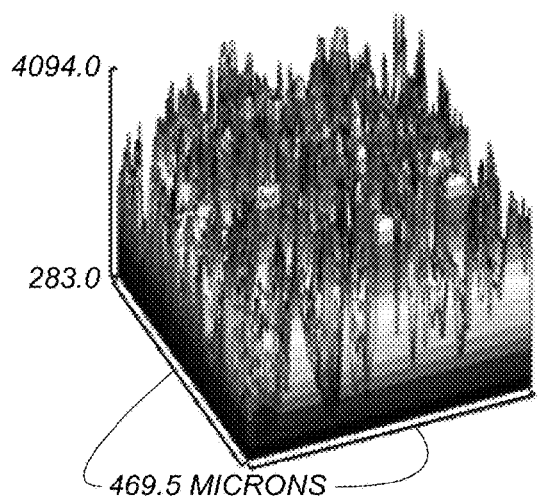
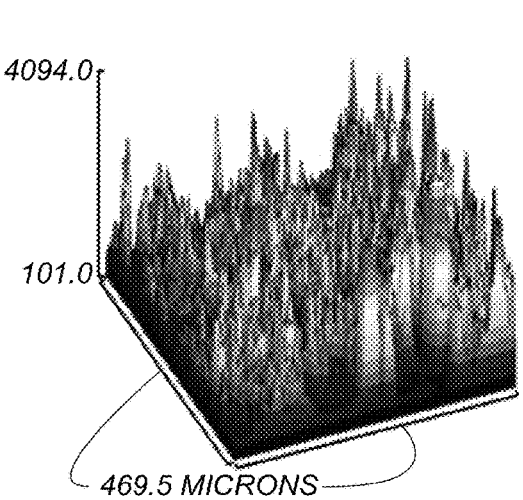
FIG. 7C  FIG. 7D

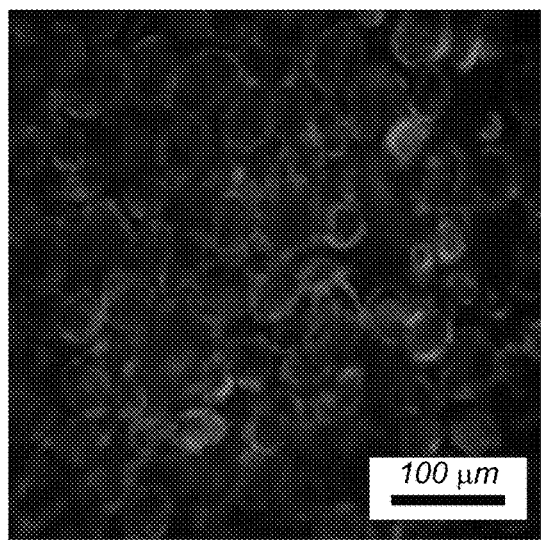
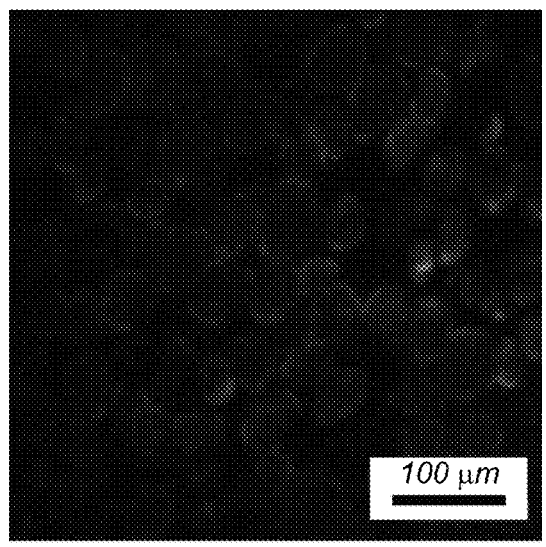
*FIG. 8A*          *FIG. 8B*
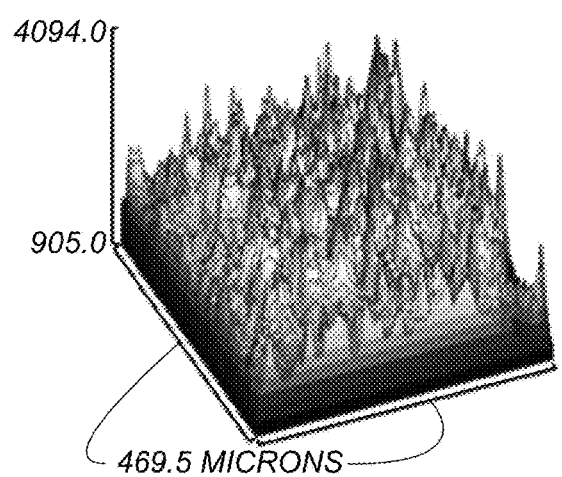
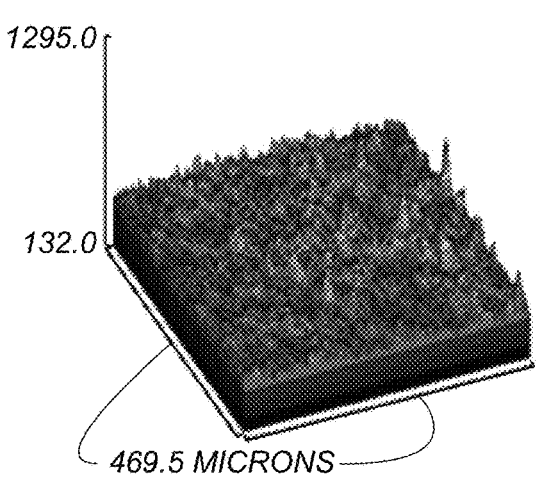
*FIG. 8C*          *FIG. 8D*

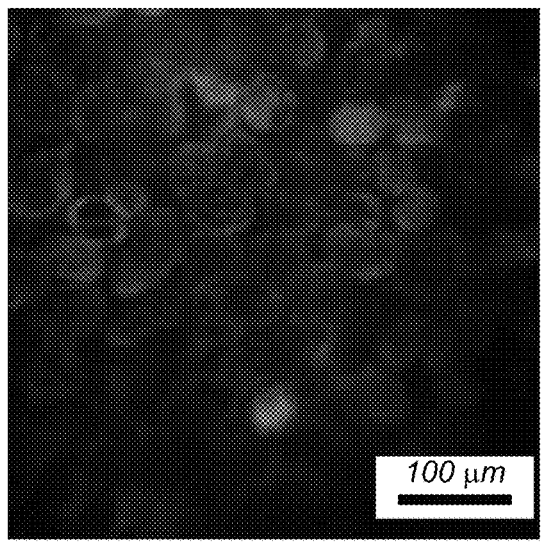
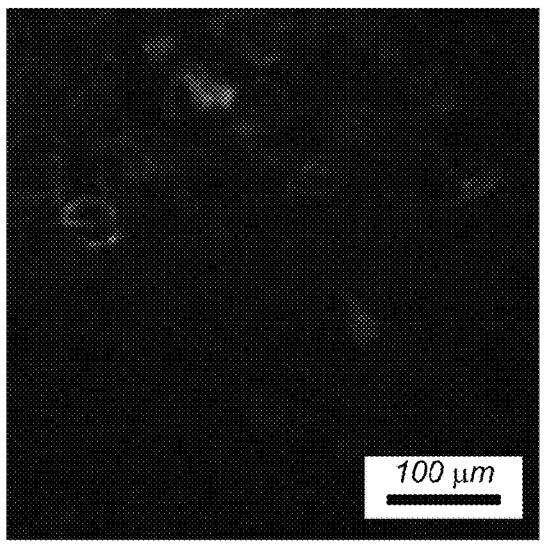
FIG. 9A     FIG. 9B
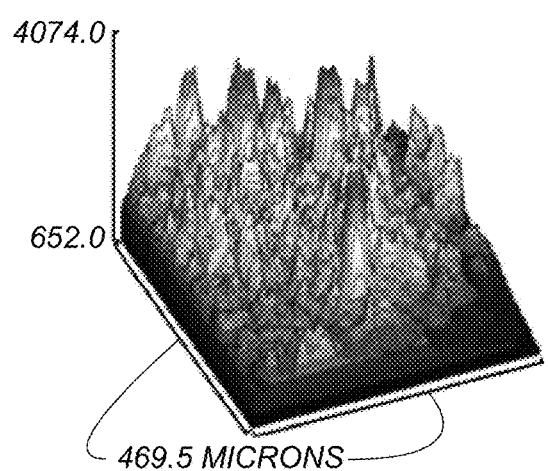
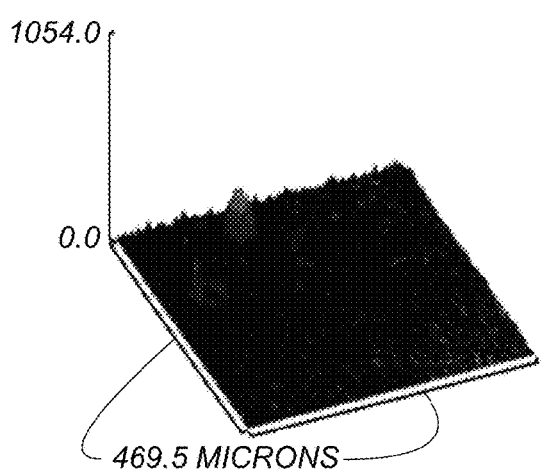
FIG. 9C     FIG. 9D

METHOD OF DEEP TISSUE IMAGING USING MULTI-PHOTON EXCITATION OF A FLUOROPHORE

CROSS-REFERENCE TO RELATED APPLICATIONS

This application claims priority to and the benefit of U.S. Provisional Patent Application Ser. No. 61/956,620 (filed Jun. 13, 2013) the entirety of which is incorporated herein by reference.

STATEMENT OF FEDERALLY SPONSORED RESEARCH OR DEVELOPMENT

This invention was made with Government support under Contract number W81 XWI-I-11-1-0335 awarded by the U.S. Army Medical Research and Material Command (USAMRMC), contract number 5SC1HD068129 awarded by the Eunice Kennedy Shriver National Institute of Child Health & Human Development, contract number 2G12RR03060-26A1 awarded by the National Center for Research Resources and contract number 8G12MD007603-27 awarded by the National Institute on Minority Health Disparities from the National Institutes of Health. The government has certain rights in the invention.

BACKGROUND OF THE INVENTION

The subject matter disclosed herein relates to imaging of biological tissues using fluorescence from intrinsic and/or extrinsic agents. One of today's main challenges of the biomedical optical community is to image deeper into a layer of biological tissue. Choosing the appropriate imaging wavelength according to light attenuation caused by tissue provides a means of increasing the imaging depth. There are "optical windows" (also known as therapeutic windows) for biological tissues in the far-red to near infrared (NIR) range which allows light to penetrate deep into tissue. In the ultraviolet to visible, the limitation of imaging depth in tissue is due to the scattering owing to extracellular and nuclear structures and attenuation of blood, e.g. oxyhemoglobin ($HbO_2$) and deoxyhemoglobin (Hb) and water. There is a first optical window between about 650 nm and about 1100 nm. There is a second window between about 1200 nm and about 1350 nm. There is a third optical window between about 1550 nm to 1800 nm. In the second and third optical windows scattering is reduced but absorption is larger. The diffusive component is reduced in the second and third windows.

The penetration depth of current imaging techniques are still limited by the scattering of the operating light in the visible range and re-absorption of the emitted light. For instance the dye fluorescein, excited by a Ti:sapphire laser beam at 800 nm, emits at 521 nm which is in the visible range. Additionally, visible intrinsic fluorescence such as tryptophan, collagen, elastin, flavins and NADH restricts molecular imaging with exogenous contrast agents, particularly when target concentrations are low emit below 600 nm from 340 nm to 520 nm.

It would be desirable to provide alternative methods of optically imaging biological tissues at a greater depth. To date, no method has been entirely satisfactory. The discussion above is merely provided for general background information and is not intended to be used as an aid in determining the scope of the claimed subject matter.

BRIEF DESCRIPTION OF THE INVENTION

In a first embodiment, a method for imaging tissue using a multi-photon process is provided In the method, both excitation and emission wavelengths fall within an optical window. The method comprises sequential steps of irradiating a fluorescent agent with a multi-photon excitation wavelength, the step of irradiating being performed with a laser with at least picosecond or faster pulses. The fluorescent agent is present within a biological tissue and has a first singlet energy gap ($S_0$ to $S_1$) corresponding to an emission wavelength between about 650 nm and about 1100 nm and an excited singlet energy gap ($S_0$ to $S_n$, where n is greater than 1) corresponding to the multi-photon excitation wavelength that is within an optical window. The step of irradiating produces an excited singlet state ($S_n$) that is higher in energy than a first singlet state ($S_1$) of the fluorescent agent. The excited singlet state ($S_n$) is permitted to undergo non-radiative relaxation to the first singlet state ($S_1$). The first singlet state ($S_1$) is permitted to undergo fluorescence to a ground state ($S_0$) to produce the emission wavelength, the emission wavelength corresponding to the first singlet energy gap ($S_0$ to $S_1$). The biological tissue is imaged using the emission wavelength to produce an image of the biological tissue.

In a second embodiment, a method for imaging tissue using a multi-photon process is provided. In the method, both excitation and emission wavelengths fall within an optical window. The method comprises sequential steps of providing indocyanine green (ICG) to a biological tissue and irradiating the ICG with a multi-photon excitation wavelength, the step of irradiating being performed with a laser with at least picosecond or faster pulses. The ICG is present within a biological tissue and has a first singlet energy gap ($S_0$ to $S_1$) corresponding to an emission wavelength between about 650 nm and about 1100 nm and an excited singlet energy gap ($S_0$ to $S_n$, where n is greater than 1) corresponding to the multi-photon excitation wavelength that is within an optical window, the step of irradiating producing an excited singlet state ($S_n$) that is higher in energy than a first singlet state ($S_1$) of the ICG. The excited singlet state ($S_n$) is permitted to undergo non-radiative relaxation to the first singlet state ($S_1$). The first singlet state ($S_1$) is permitted to undergo fluorescence to a ground state ($S_0$) to produce the emission wavelength, the emission wavelength corresponding to the first singlet energy gap ($S_0$ to $S_1$). The biological tissue is imaged using the emission wavelength to produce an image of the biological tissue.

In a third embodiment, a method for imaging tissue using a multi-photon process is provided. In the method, both excitation and emission wavelengths fall within an optical window. The method comprises sequential steps of irradiating a fluorescent agent with a multi-photon excitation wavelength having n photons, where n is two or more, the multi-photon excitation wavelength being within an optical window between about 650 nm to about 1100 nm or between about 1200 nm to about 1350 nm or between about 1550 nm to 1800 nm. The step of irradiating is performed with a laser with at least picosecond or faster pulses. The fluorescent agent is present within a biological tissue and has a first singlet energy gap ($S_0$ to $S_1$) corresponding to an emission wavelength between about 650 nm and about 1100 nm, wherein the step of irradiating produces a first singlet state ($S_1$) of the fluorescent agent. The first singlet state ($S_1$) is permitted to undergo fluorescence to a ground state ($S_0$) to produce the emission wavelength, the emission wavelength corresponding to the first singlet energy gap ($S_0$ to $S_1$). The biological tissue is imaged using the emission wavelength to produce an image of the biological tissue.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 1A depicts the optical attenuation of principal tissue chromophores in the spectral region of 300 to 2500 nm while

FIG. 4 is a table listing examples of fluorescent agents in optical window emitting pumped into $S_2$ and/or $S_1$;

FIG. 7A is a multi-photon microscopy image of a spinach leaf at 685 nm, FIG. 7B is a control image at 525 nm, FIG. 7C is a surface plot of light intensity from FIG. 7A while FIG. 7D is a surface plot of light intensity from FIG. 7B;

FIG. 8A is a multi-photon microscopy image of a spinach leaf at 685 nm with 200 micrometer-thick rat brain covering the leaf; FIG. 8B is a control image at 525 nm; FIG. 8C is a surface plot of light intensity from FIG. 8A while FIG. 8D is a surface plot of light intensity from FIG. 8B;

FIG. 9A is a multi-photon microscopy image of a spinach leaf at 685 nm with 400 micrometer-thick rat brain covering the leaf; FIG. 9B is a control image at 525 nm; FIG. 9C is a surface plot of light intensity from FIG. 9A while FIG. 9D is a surface plot of light intensity from FIG. 9B;

FIG. 10C is a surface plot of light intensity from FIG. 10A while FIG. 11A is a graph showing average integrated peak intensities for the testing and control images while

DETAILED DESCRIPTION OF THE INVENTION

Disclosed in this specification is a method to enhance imaging depth in biological tissue. An ultrafast laser causes a fluorescent agent to undergo a multi-photon (e.g. two-photon or three-photon) excitation to an excited singlet state ($S_n$, wherein n is greater than 1) that is higher energy than the first singlet state ($S_1$) wherein both the excitation and emission wavelengths are within an optical window. The one embodiment, the excited singlet state is the second singlet ($S_2$) state. The fluorescent agent undergoes an ultrafast, non-radiative relaxation from $S_n$ to $S_1$ followed by fluorescent emission from its first singlet state ($S_1$) to ground ($S_0$). The fluorescent agent is selected to have an emission wavelength within an optical window corresponding to its first singlet ($S_1$) to ground state ($S_0$) transition. The multi-photon excitation wavelength (e.g. $S_0$ to $S_2$) and the emission wavelength ($S_1$ to $S_0$) are both within the optical window for deeper tissue penetration. Unlike the conventional two photon microscopy techniques, which can just make either the excitation or emission wavelength fall in the optical window, but not both of them, the disclosed method combines (a) the advantages of rapid non-radiative relaxation from $S_n$ to $S_1$ and (b) drives the wavelengths of both excitation and emission of the imaging agents to fall in the optical window. This enhances the imaging depth, diminishes the scattering cause by short wavelengths, and decreases the out-of-focus background associated with single-photon excitation over conventional fluorescence microscope. Since both the multi-photon excitation and emission fall in the "optical window" the method can be used for in vivo imaging of microvessel in brain tissue, gastrointestinal (GI) track tissue, breast tissue, kidney tissue, prostate tissue, heart tissue and other deep organs. The fluorescent agent may be introduced into a blood vessel of a biological organism by, for example, intravenous means. In one embodiment, two-dimensional images are produced. In another embodiment, three-dimensional images are produced. Longer wavelengths are suitable for multi-photon femtosecond laser pumping to $S_1$, $S_2$ or upper $S_n$ states (e.g. n=3). The $S_2$ or upper $S_n$ states relax to $S_1$ for emission. In one embodiment, a two photon pumping to $S_1$ is performed using a multi-photon excitation wavelength between 1600 nm and 1700 nm from an erbium fiber, supercontinuum source or optical parametric oscillator. For example, indocyanine green (ICG) adsorbs by a two photon process into $S_2$ at about 840 nm and emits at about 820 nm and about 685 nm. ICG also adsorbs by a two photon process into $S_1$ at about 1600 nm and emits at about 820 nm and 685 nm. When used in this specification concerning the recitation of wavelengths, the term "about" generally refers to a wavelength within 25 nm of the specified wavelength.

Figure 1A:
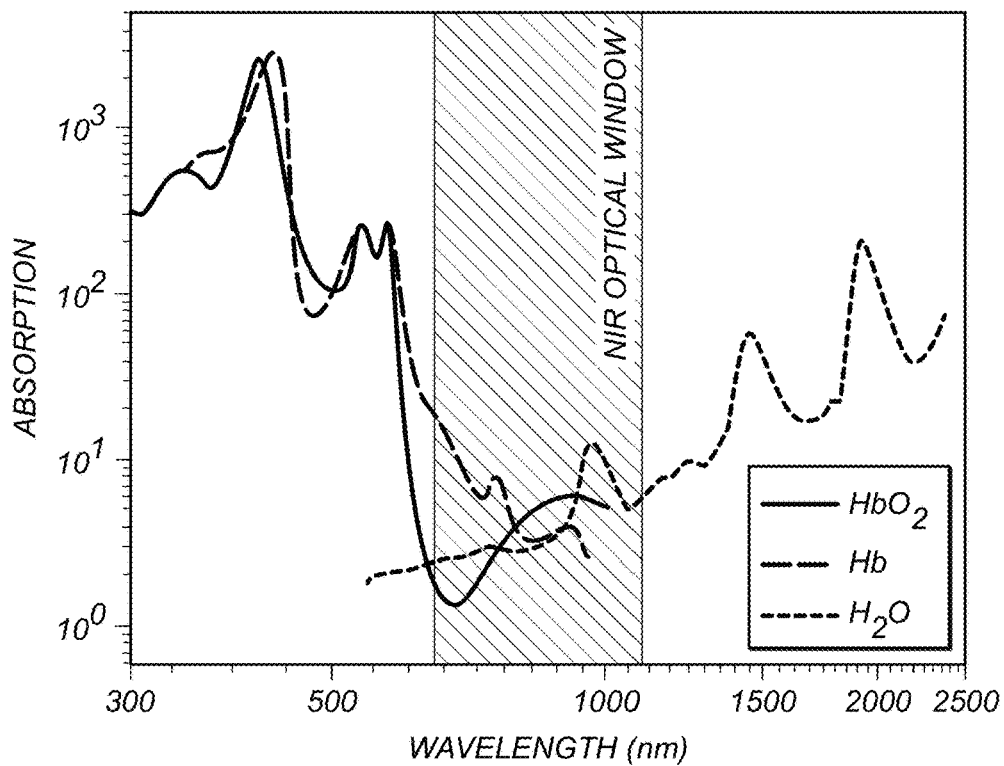
Figure 1B:
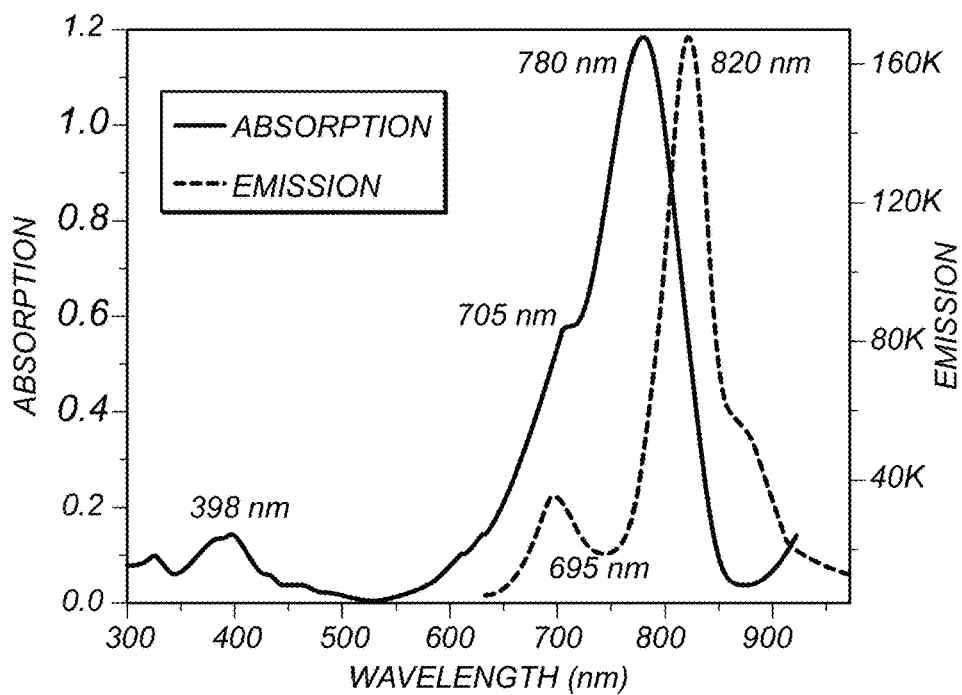
FIG. 1B shows the absorption (solid line) and fluorescence (dashed line) spectra of Indocyanine green (ICG)

FIG. 1A depicts the optical attenuation of principal tissue chromophores in the spectral region of 300 to 2500 nm. A first optical window is shown between 650 nm and 1100 nm. FIG. 1B shows the absorption (solid line) and fluorescence (dashed line) spectra of Indocyanine green (ICG). ICG shows an absorption maximum at 780 nm that can be pumped by a 840 nm (first optical window) laser light to $S_2$ while avoiding irradiating at the emission wavelength at about 820 nm (first optical window) from $S_1$. Alternatively ICG can be pumped to $S_1$ by a 1600 nm (third optical window) laser light by a two-photon process and emit at about 820 nm (first optical window). In both cases, both the absorption and emission are in optical windows. The dilemma is overcome by having both the exciting and imaging wavelengths in the NIR optical window is illustrated by FIG. 1B. FIG. 1B shows the absorption spectrum (solid line) and the emission spectrum (dot line) of ICG.

Figure 2:
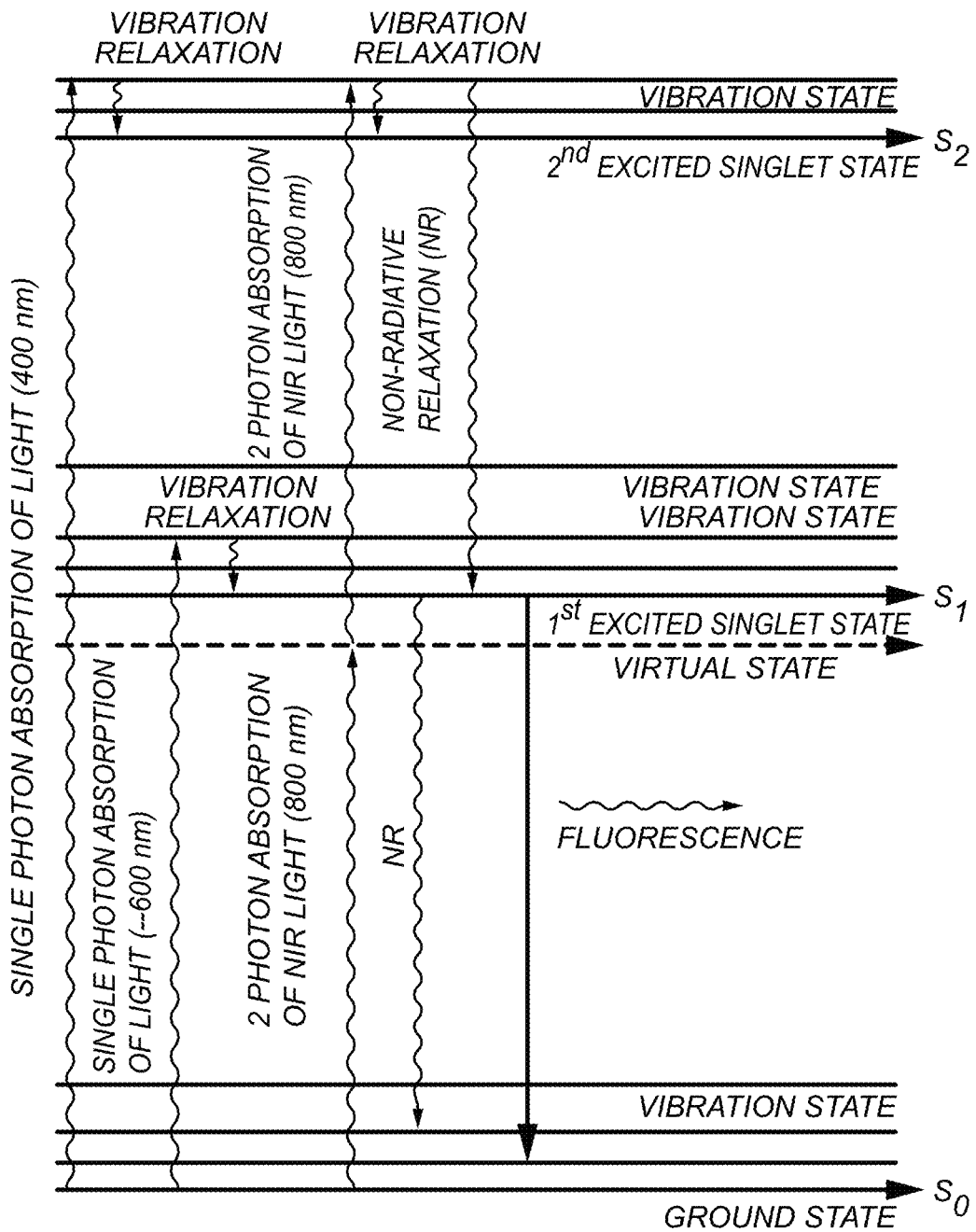
FIG. 2 is a Jablonski energy level diagram for Chlorophyll α (Chl α) to be pumped to first and second excited singlet states by a one- or two-photon absorption.
Figure 3:
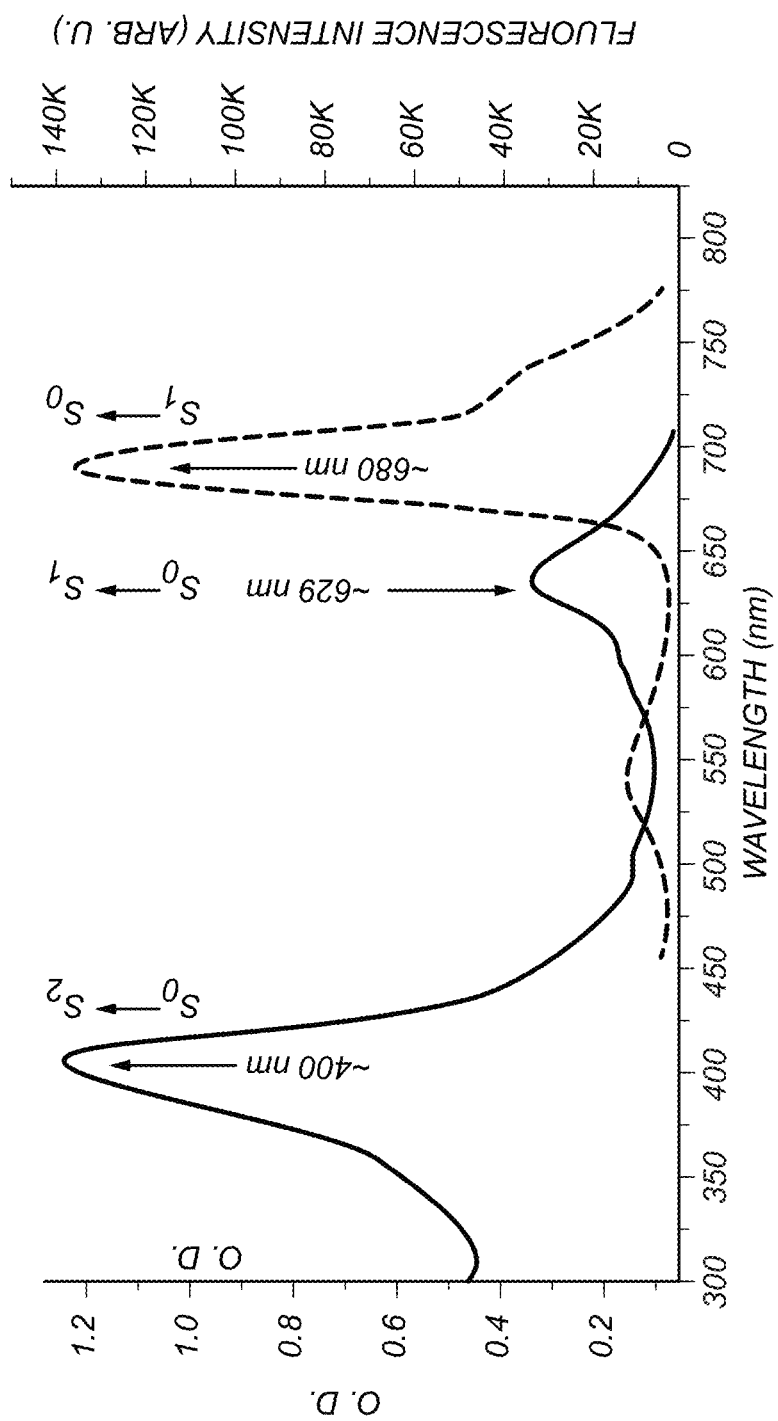
FIG. 3 illustrates measured absorption (solid line) and fluorescence (dot line) spectra of Chl α.

FIG. 2 and FIG. 3 illustrate the mechanism of one photon and two photon excitation of $S_1$ and $S_2$ bands of Chlorophyll α (Chl α) using a Jablonski energy level diagram (FIG. 2) and the measured fluorescence and absorption spectra (FIG. 3) of Chl α. The absorption spectrum (solid line) was measured using UV-VIS-NIR spectrophotometer (Cary 500 Scan) and the emission spectrum (dot line) was acquired by FluoroMax-3 spectrometer (Horiba Jobin Yvon). The absorption of photons drives Chl α to either excited $S_1$ or $S_2$ state. Chl α excitation can be achieved by red light at about 629 nm band (weakly absorbing, $S_1$ produced) or by violet light at about 404 nm (Soret band, outside of the NIR optical window, $S_2$ produced). The photo-excited Chl α decays to the ground state by emitting photons (about 680 nm) from $S_1$. The salient relaxation process behind the use of multi-photon $S_2$ excitation is an ultrafast, non-radiative relaxation process from $S_2$ to $S_1$.

Exemplary fluorescent agents include Chl α and ICG. Chl α is vital for photosynthesis, easy to obtain and non-toxic. ICG is one of the most important medical imaging agents since it is the only U.S. Food and Drug Administration (FDA)-approved dye in NIR range. The multi-photon $S_2$ excitation of these fluorescent agents using Ti:Sapphire laser at about 800 nm makes it possible to force wavelengths of both excitation and emission of the imaging agents to fall in the NIR tissue window. In those embodiments, where the fluorescent agent is extrinsic the agent may be added as a dilute solution (in vitro embodiments) or by injection (in vivo embodiments) such as with an intravenous drip or the like.

ICG was purchased from MP Biomedicals, LLC (Solon, Ohio 44139) and Chl α was extracted from fresh spinach leaves using ethyl alcohol. Chl α strongly absorbs red and blue-violet light from $S_1$ and $S_2$ bands, respectively. ICG and its derivative dyes (Cypate, Cybesin, and Cytate etc.) are used in cancer detection, surgery cancer margin assessment, and optical vessel imaging. The potential of ICG $S_2$ excitation is possible since a weak $S_2$ band exists at about 398 nm and dual fluorescence peaks at 695 nm (weak) and 820 nm (strong) were observed. ICG is among the family of dichromic fluorescent dyes.

Multiphoton Microscopy System (Prairie Tech., Inc., W.I.) with Coherent Ultima 130 femtosecond duration laser pulse light source was used to investigate multi-photon $S_2$ excitation of Chl α and ICG. The multi-photon excitation at 800 nm (for Chl α) was used to achieve a $S_2$ band of 400 nm to accomplish fluorescence around 680 nm for both Chl α and ICG. This is the optimal condition for the study of multi-photon $S_2$ excitation of Chl α because of the strong absorption of $S_1$ band at about 404 nm and strong emission at about 680 nm of Chl α as shown in FIG. 3. The weaker emission of ICG at about 695 nm was chosen due to equipment limitations. Specifically, the un-removable IR block filter in front of the photomultiplier tube (PMT) of the multi-photon microscopy Prairie system cut the strong emission of ICG at about 820 nm and only allows the visible light pass through. Alternative wavelengths may be used when other equipment is used.

The multi-photon $S_2$ excitation properties of two fluorescent agents, Chl α and ICG, were characterized using the multi-photon microscopy technique. The strong emission intensities of multi-photon microscope images of Chl α- and ICG-stained beads were observed under the imaging channel of 685 nm, which indicates they can be used to as potential $S_2$ multi-photon fluorescent agents to enhance the imaging depth. The unique spectral characteristics of Chl α and ICG demonstrate that their superior multi-photon $S_2$ excitation optical properties may be utilized for multi-photon microscopy-based histological studies of thick tissue and/or multi-photon in vivo imaging.

There are many fluorescent agents with similar spectral profiles as Chl α and ICG that can be used as potential $S_2$ multi-photon fluorescent agents. Cyanine and ICG-derivative dyes have similar spectral characteristics, such as cypate, cybesin and cytate can also be used as potential multi-photon $S_2$ fluorescent biomarker agents; especially, the latter two dyes, e.g. cybesin and cytate, are smart dyes which can target bombesin and somatostatin receptors overexpressed on cancer cells, respectively. Extensive absorption and emission spectra of dyes agents have been studied by Oregon Medical Laser Centre. All these fluorescent agents (ICG with dual emission) have stronger absorption $S_2$ band or even higher singlet ($S_n$) state over the $S_1$ band. Although their toxicity is still needed to be investigated, spectral characteristics of other fluorescent agents are listed in the table of FIG. 4 and such agents are contemplated for use with the disclosed method.

EXAMPLES

The specimens to be imaged were Chl α- and ICG-stained uncoated pore glass beads (37 micrometer with pore diameter of about 24 nm). The beads were respectively soaked in a Chl α and ICG solution overnight. All the sample preparations and measurements were performed at room temperature. The size of beads was selected to approximate microvessels in a human brain.

Figure 5:
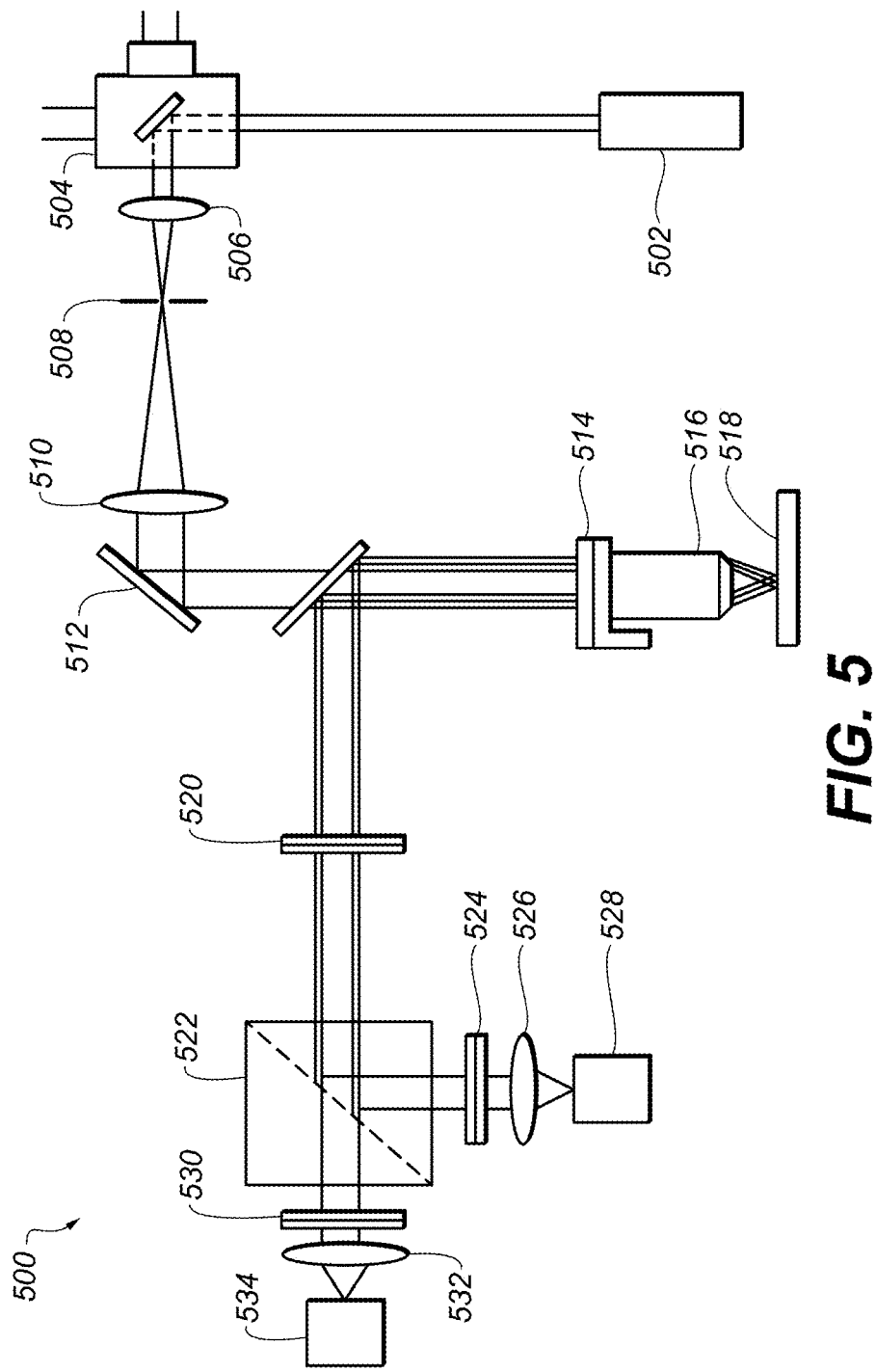
FIG. 5 is a schematic illustration of a system used to produce the examples of FIGS. 6A-6H.

FIG. 5 is a schematic diagram of a system 500 for imaging. A picosecond or faster laser 502 (e.g. a Ti:Sa laser) provides a multi-photon wavelength to galvanometer-drive X-Y mirror 504. The multi-photon wavelength is passed through a scan lens 506, a field aperture plane 508 and through a tube lens 510. A mirror 512 directs the multi-photon wavelength to a piezoelectric translator 514 which is in communication with objective lens 516 and specimen 518. An emission wavelength is produced by specimen 518 which is subsequently directed to IR-blocking filter 520. IR-blocking filter 520 selects wavelengths between 400 and 700 nm. A dichroic photomultiplier tube 522 is provided that splits the emission wavelength into two beams. The first beam (control) is passed through a band filter 524 that is selective for a control wavelength (e.g. 525±35 nm). The first beam passes through a tube lens 526 before being detected at photomultiplier tube 528. The second beam is passed through a band filter 530 that is selective for the emission wavelength (e.g. 685±40 nm). The second beam passes through a tube lens 532 before being detected at photomultiplier tube 534.

The multi-photon microscopy of Chl α and ICG-stained beads were imaged under a channel outfitted with wide band filter of ET 685±40 nm with a 40× lens (N.A.=0.8, water immersion, Olympus). Control images were taken by another channel with filter of ET 525±35 DM (aroma) for control study while other imaging parameters (such as laser power, amplification of the PMT, and scanning speed etc.) were kept constant between control (525 nm) and imaging (685 nm) channel.

Figure 6D:
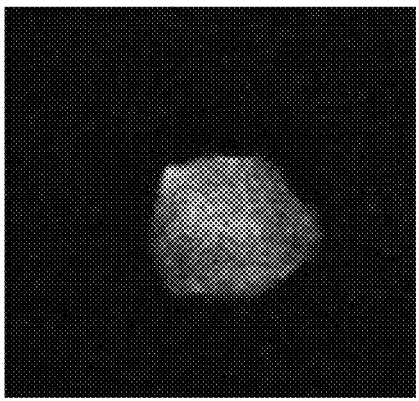
FIG. 6C is the multi-photon microscope image of ICG-stained beads (685 nm) and FIG. 6D is the multi-photon microscope image of a control (525 nm) channel.
Figure 6C:
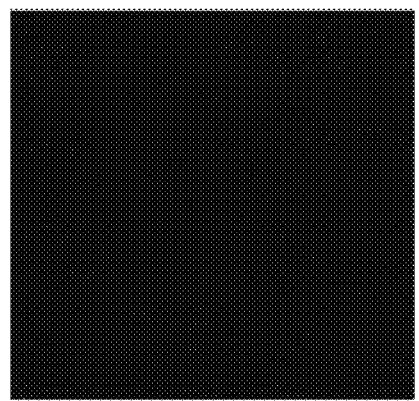
Figure 6B:
FIG. 6B is the multi-photon microscope image of control (525 nm) channel.
Figure 6A:
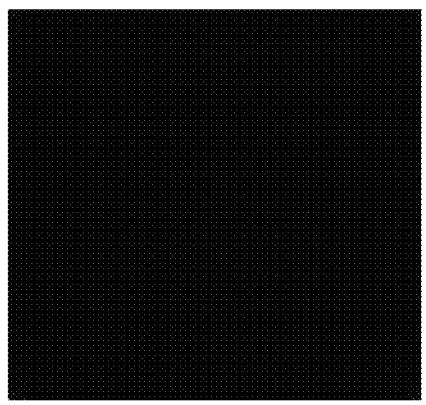
FIG. 6A is the multi-photon microscope image of Chl α-stained beads under imaging (685 nm)
Figure 6H:
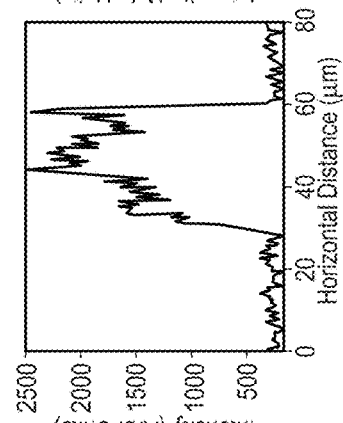
FIG. 6E, FIG. 6F, FIG. 6G and FIG. 6H are the corresponding digital spatial cross section intensity distribution of the image shown in FIG. 6A, FIG. 6B, FIG. 6C and FIG. 6D, respectively.
Figure 6G:
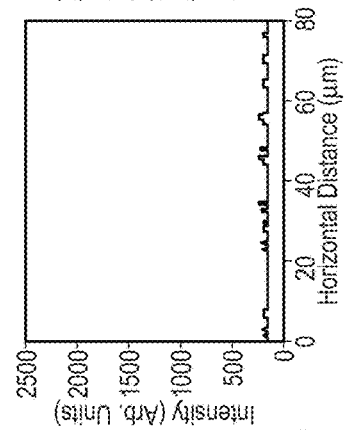
Figure 6F:
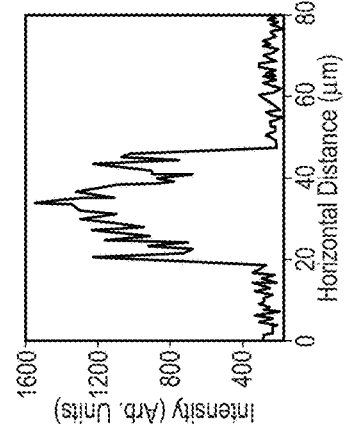
Figure 6E:
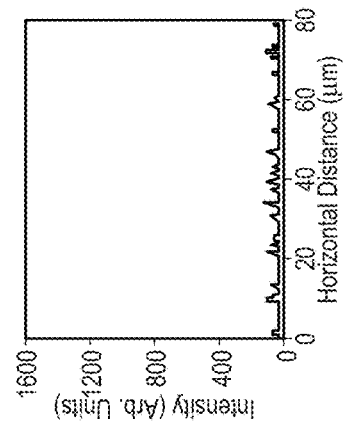

FIG. 6A and FIG. 6B show the multi-photon microscopy images of Chl α-stained beads under imaging and control channel, respectively. The multi-photon microscope images of ICG-stained beads under imaging and control channel were displayed in FIG. 6C and FIG. 6D, respectively. The potential application of Chl α and ICG for $S_2$ multi-photon imaging was validated by observing the fluorescence images of the Chl α- and ICG-stained beads under the channel of 685 nm, which is close to the emission peak of Chl α and ICG. No fluorescence images of beads could be acquired under the control channel of 525 nm, which is far from the emission peak of Chl α and ICG. The multi-photon microscopy images of Chl α- and ICG-stained beads can be clearly seen under the imaging channel, but no visible profiles of bead are under the control channel. The emission intensity of the Chl α- and ICG-stained beads under the imaging channel is much higher than that under the control channel. This property can be more clearly visualized by FIG. 6E, FIG. 6F, FIG. 6G and FIG. 6H, which is the digital spatial cross section of intensity distribution of the image shown in FIG. 6A, FIG. 6B, FIG. 6C and FIG. 6D. These results show that the optimized multi-photon microscopy imaging of Chl α- and ICG-stained beads under multi-photon excitation of 800 nm and 840 nm, respectively nm is the channel of 685 nm, which is exactly the strong fluorescence peak of Chl α, and close to the second strong emission peak of ICG at 685 nm and emission at 820 nm for ICG. This indicates that the recorded microscope image is indeed formed from emission of the $S_2$ multi-photon fluorescent agent. Therefore, Chl α and ICG can be used as potential $S_2$ multi-photon fluorescents agent to enhance the imaging depth using multi-photon microscopy.

Brain Tissue Examples

A Wistar rat (P10) was decapitated and the brain was transferred into a chilled oxygenated Ringer solution containing 126 mM NaCl; 2.5 mM KCl; 1.25 mM $NaH_2PO_4$; 2 mM $CaCl_2$; 1 mM $MgCl_2$; 10 mM glucose; 26 mM $NaHCO_3$; 5 mM pyruvate; pH 7.40 to 7.45, and then was rapidly embedded in 2% low melting point agarose and processed for coronal sectioning using a compresstome (VF300, Precisionary Instruments). Slices were cut at the thickness of 200, 400, 450 and 500 micrometers, respectively. The brain slices were quickly transferred one at a time to a gridded container filled with oxygenated Ringer solution.

Fresh Spinach Leaf Preparation

Spinach leaves were purchased fresh from local market. Each selected fresh spinach leaf was glued on a microscope slide. The fresh leaf contained the light-absorbing molecule Chl α and plant organelle chloroplast which are essential for the photosynthetic process. It is known that Chl α strongly absorbs red and blue-violet light from $S_1$ and $S_2$ bands, respectively, to give the green color of leaves. The absorption of photons could drive the molecules of Chl α from the ground ($S_0$) state to the $S_1$ or $S_2$ excited states, converting photonic energy into electronic excitation. There are three ways to obtain the emission of Chl α in far-red light of about 680 nm, $S_1$ excitation caused by red light around 630 nm, $S_2$ excitation by violet light around 404 nm, or $S_2$ excitation by two photons around 800 nm which gives non-radiative process for $S_2$ to $S_1$ following two-photon excitation. See FIG. 2.

Sample Preparation

The brain slice was carefully placed on the fresh spinach leaf and a cover slip was placed on top of the brain tissue. Chlorophyll α in the fresh spinach leaf samples was imaged with two-photon microscopy. Experiments were conducted one by one on the 200, 400, 450 and 500 micrometer thick brain tissue covered samples, and a leaf sample without any tissue covered. All the sample preparations and measurements were performed at room temperature.

Multiphoton Microscope and Image Collection

Twelve-bit 2-D images were captured by a Multiphoton Microscopy System (Prairie Tech., Inc., WI) with Coherent Chameleon 140 femtosecond duration laser pulses light source. The excitation wavelength 800 nm was used to achieve the two photon pumping $S_2$ band of 400 nm and to accomplish fluorescence imaging in Chl α's spectral range around 680 nm. This is the optimal condition for studying 2P $S_2$ excitation of Chl α due to the strong $S_1$ band absorption and emission at 680 nm. Images of the spinach leaf were obtained by two-photon microscopy with a water immersion objective (20×, NA=0.5, Olympus) through two different PMT channels, a testing channel and a control channel outfitted with wide band filter of 685±40 nm and 525±35 nm respectively (Chroma), while other imaging parameters were kept constant.

FIG. 7A, FIG. 7B, FIG. 7C and FIG. 7D shows two-photon microscope images of the spinach leaf under testing and control channels without any brain tissue covered. Clear images of the spinach leaf at both the testing and control channels shown in FIG. 7A and FIG. 7B, respectively, indicate a strong emission peak of 685 nm under $S_2$ excitation of Chl α and the shoulder emission peak close to 525 nm. Red or green dots inside the cells were likely the chloroplast organelles which contain Chl α and other fluorescent agents. The red channel represented the two-photon $S_2$ state of Chl α and showed a much stronger peak. FIG. 7C shows the surface plot of light intensity corresponding to FIG. 7A (testing channel) while FIG. 7D shows the light intensity corresponding to FIG. 7B (control channel), neither of which are covered with brain tissue.

Figure 10A:
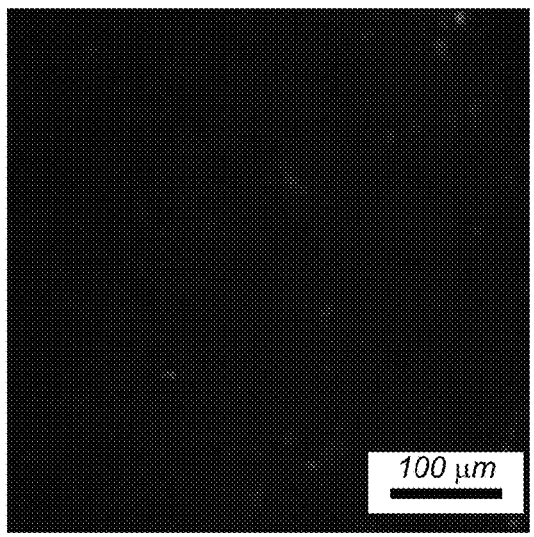
FIG. 10A is a multi-photon microscopy image of a spinach leaf at 685 nm with 450 micrometer-thick rat brain covering the leaf.
Figure 10B:
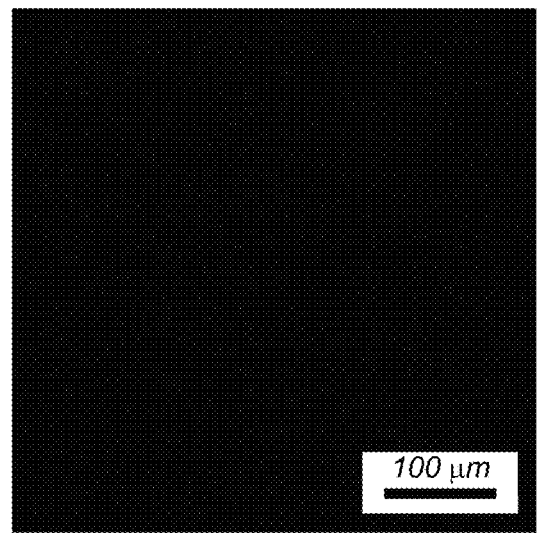
FIG. 10B is a control image at 525 nm.
Figure 10C:
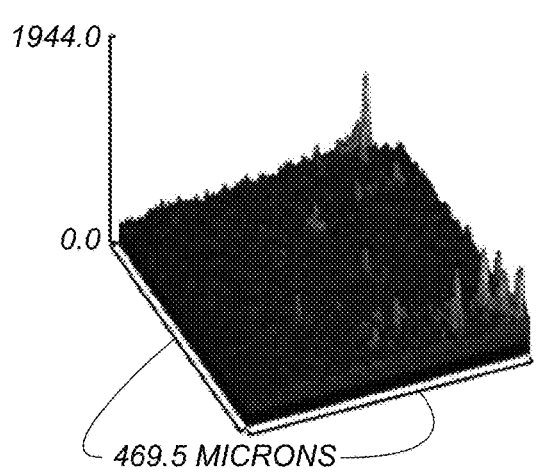
Figure 10D:
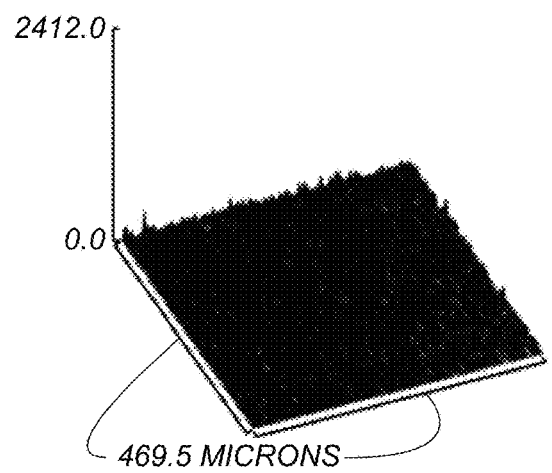
FIG. 10D is a surface plot of light intensity from FIG. 10B.

The two-photon microscope images of the spinach leaf covered with 200 micrometer freshly-cut brain slices under testing and control channel are displayed in FIG. 8A (200 micrometer image channel) FIG. 8B (200 micrometer control channel). The two-photon microscope images of the spinach leaf covered with 400 micrometer freshly-cut brain slices under testing and control channel are displayed in FIG. 9A (400 micrometer image channel) FIG. 9B (400 micrometer control channel). The two-photon microscope images of the spinach leaf covered with 450 micrometer freshly-cut brain slices under testing and control channel are displayed in FIG. 10A (450 micrometer image channel) FIG. 10B (450 micrometer control channel). Corresponding surface plots of light intensity are shown in FIG. 8C (image), FIG. 8D (control), FIG. 9C (image), FIG. 9D (control), FIG. 10C (image) and FIG. 10D (control).

The two photon microscopy images of Chl α can be clearly observed under the testing channel with 200 or 400 micrometer brain tissue on top, but others cannot be clearly distinguished as those under the control channel. With 450 micrometer brain tissue covered on top, the testing channel shows some vague profiles of Chl α but no visible profile in the control channel, which indicates that brain tissue with thickness of 450 micrometers is the maximum penetration depth for the Chl α at $S_2$ state under current experimental environment.

Moreover, the much stronger emission intensity of the Chl α under the testing channel over the control channel can be more clearly visualized in the surface plots of light intensity (FIGS. 8C, 8D, 9C, 9D, 10C and 10D). These surface plot results show that the optimized two photon microscopy imaging of Chl α at 685 nm was exactly the strong fluorescence peak of Chl α under the two photon $S_2$ state, indicating that the $S_2$ state fluorescent imaging of Chl α leads to an excellent tissue penetration depth for up to 450 micrometers, with much better quality than the control channel. Although the scattering properties of the brain tissue were likely changed shortly after it was cut into slices, the experiment was conducted in an acute way to keep the maximum penetration depth limited variation with sufficient oxygenated environment, to avoid a reduction in the maximum penetration depth. Therefore, the technique of combining two photon and $S_2$ states to achieve deep tissue imaging can be further optimized and tested with in vivo experiments of the brain vasculature and neural structures.

Figure 11A:
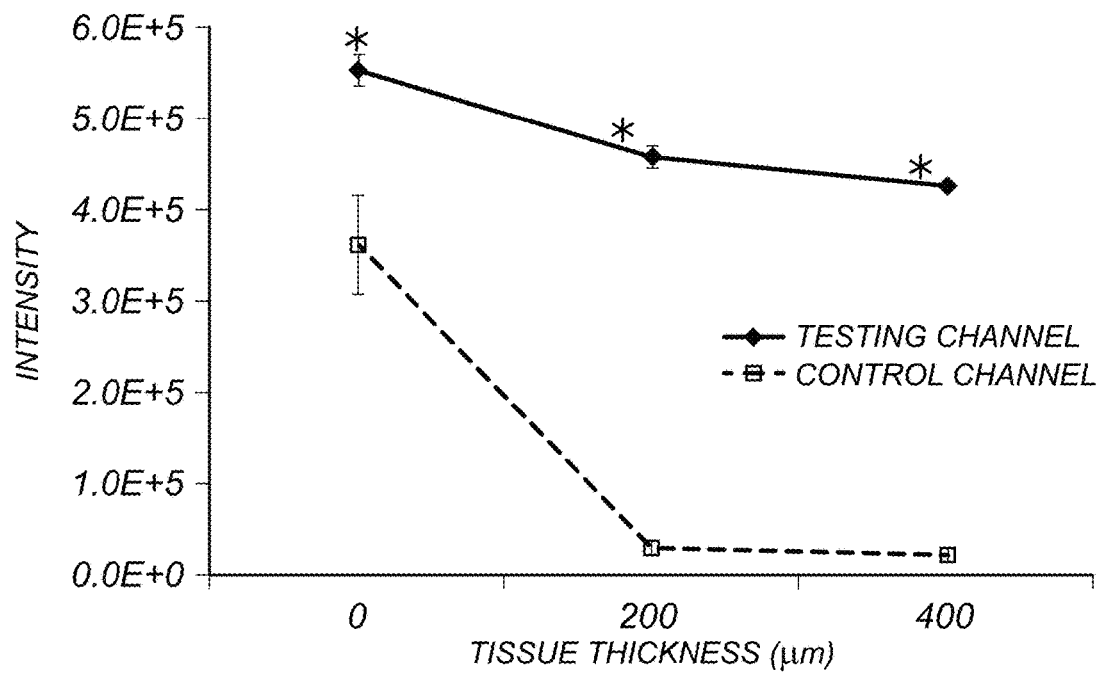
Figure 11B:
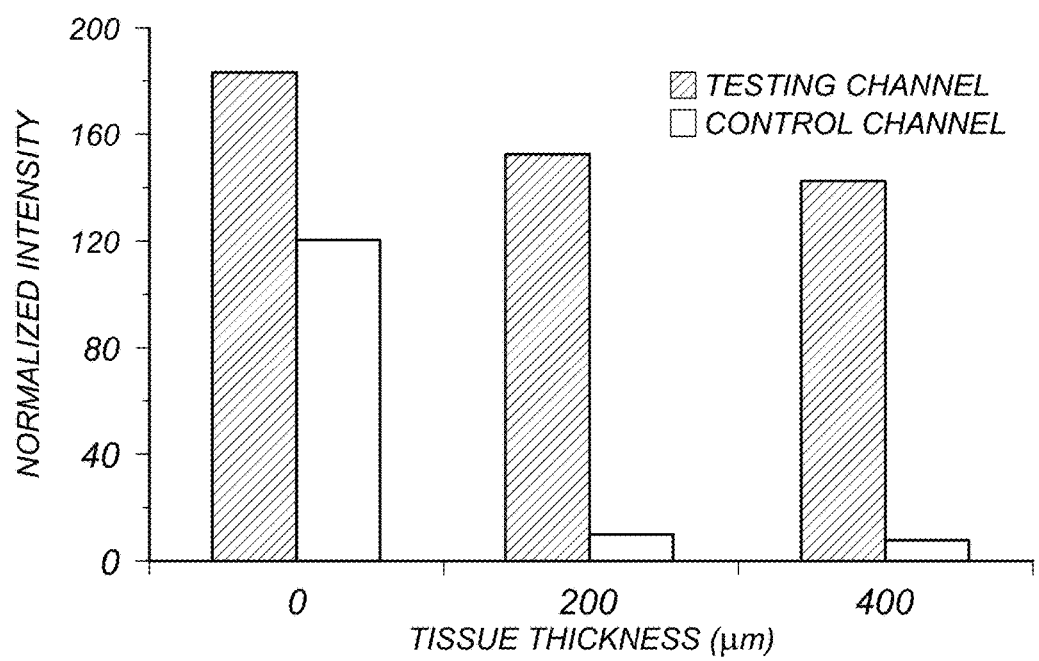
FIG. 11B is a graph showing the normalized intensity for the testing and control images.

In order to quantify the emission penetrated through the tissue, five different regions of interest (ROI) with peak intensity were selected and the same five ROI were also selected from the background correspondingly. The integrated light intensity of each region was calculated separately, and then averaged for each image as $I_{peak}$ and $I_{background}$. FIG. 11A shows that the averaged integrated peak intensities in the testing and control images have significant differences (p<0.001). FIG. 11B shows the normalized intensity:

$$I_{normalized} = \frac{I_{peak} - I_{background}}{I_{background}} \quad \text{(equation 1)}$$

for each image group. The control channel's intensity dropped tremendously from 120.1 without covering tissue to 7.5 with 400 micrometer tissue cover. However, the testing channel's intensity dropped from 183.6 without covering tissue to 141.4 with 400 micrometer tissue covered.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for imaging tissue using a multi-photon process where both excitation and emission wavelengths fall within an optical window, the method comprising sequential steps of:
    irradiating a fluorescent agent with a multi-photon excitation wavelength that is within the optical window, wherein the optical window is selected from a group consisting of:
        a first optical window at 650±25 nm to 1100±25 nm;
        a second optical window at 1200±25 nm to 1350±25 nm; and
        a third optical window at 1550±25 nm to 1800±25 nm;
    the step of irradiating being performed with a laser with picosecond pulses,
    the fluorescent agent being present within a biological tissue and having:
        a first singlet energy gap ($S_0$ to $S_1$) corresponding to an emission wavelength within the optical window; and
        an excited singlet energy gap ($S_0$ to $S_n$ where n is greater than 1) corresponding to the multi-photon excitation wavelength that is within the optical window, the step of irradiating producing an excited singlet state ($S_n$) that is higher in energy than a first singlet state ($S_1$) of the fluorescent agent;
    allowing time to pass such that the excited singlet state ($S_n$) is permitted to undergo non-radiative relaxation to the first singlet state ($S_1$);
    allowing time to pass such that the first singlet state ($S_1$) is permitted to undergo fluorescence to a ground state ($S_0$) to produce the emission wavelength that is within the optical window, the emission wavelength corresponding to the first singlet energy gap ($S_0$ to $S_1$); and
    imaging the biological tissue using the emission wavelength to produce an image of the biological tissue.

2. The method as recited in claim 1, wherein the fluorescent agent is selected from the group consisting of chlorophyll and indocyanine green (ICG).

3. The method as recited in claim 1, wherein the image of the biological tissue is a two-dimensional image.

4. The method as recited in claim 1, wherein the image of the biological tissue is a three-dimensional image.

5. The method as recited in claim 1, wherein the optical window is 700±25 nm to 900±25 nm and both the emission wavelength and the multi-photon excitation wavelength are within the optical window.

6. The method as recited in claim 1, wherein the excited singlet state ($S_n$) is a second singlet state ($S_2$) and the multi-photon excitation wavelength is a two-photon or three-photon wavelength.

7. The method as recited in claim 1, further comprising passing the emission wavelength through a filter that is selective for the emission wavelength, the step of passing being performed prior to the step of imaging the biological tissue.

8. The method as recited in claim 1, wherein the fluorescent agent is selected from the group consisting of cypate, cybesin and cytate.

9. The method as recited in claim 1, wherein the fluorescent agent is selected from the group consisting of diprotonated-tetraphenylporphyrin, magnesium octaethylporphyrin, N-confused tetraphenylporphyrin, octaethylporphyrin, pheophorbide A, porphin, pyropheophorbide A methyl ester, pyropheophorbide A, TBP-beta-octa(COOBu)-Fb, TBP-beta-octa(COOBu)-Zn, TBP-meso-tetra(4-COOMe-phenyl)-Fb, TBP-meso-tetra(4-COOMe-phenyl)-Zn, Tetrakis(2,6-dichlorophenyl) porphyrin, Tetrakis (o-aminophenyl) porphyrin, and Tetramesitylporphyrin.

10. The method as recited in claim 1, wherein the multi-photon excitation wavelength is within the optical window of 700±25 nm to 1100±25 nm.

11. The method as recited in claim 1, wherein the multi-photon excitation wavelength is within the optical window of 1200±25 nm to 1350±25 nm.

12. The method as recited in claim 1, wherein the multi-photon excitation wavelength is within the optical window of 1550±25 nm to 1800±25 nm.

13. The method as recited in claim 1, wherein the biological tissue is imaged at a depth greater than 200 µm.

14. The method as recited in claim 1, wherein the multi-photon excitation wavelength is 1600 nm.

15. The method as recited in claim 1, wherein the multi-photon excitation wavelength is 800 nm.

16. The method as recited in claim 1, wherein the biological tissue is in vivo.

17. The method as recited in claim 16, wherein the biological tissue is human or animal tissue selected from the group consisting of brain tissue, breast tissue, kidney tissue, prostate tissue, gastrointestinal tissue and heart tissue.

18. The method as recited in claim 16, further comprising introducing the fluorescent agent into a blood vessel of a biological organism.

19. A method for imaging tissue using a multi-photon process where both excitation and emission wavelengths fall within an optical window of 700±25 nm to 900±25 nm, the method comprising sequential steps of:
   providing indocyanine green (ICG) to a biological tissue;
   irradiating the ICG with a multi-photon excitation wavelength of 800 nm, the step of irradiating being performed with a laser with picosecond pulses, the ICG being present within a biological tissue and having:
      a first singlet energy gap ($S_0$ to $S_1$) corresponding to an emission wavelength of 685 nm; and
      an excited singlet energy gap ($S_0$ to $S_n$ where n is greater than 1) corresponding to the multi-photon excitation wavelength of 800 nm that is within the optical window, the step of irradiating producing an excited singlet state ($S_n$) that is higher in energy than a first singlet state ($S_1$) of the ICG;
   allowing time to pass such that the excited singlet state ($S_n$) is permitted to undergo non-radiative relaxation to the first singlet state ($S_1$);
   allowing time to pass such that the first singlet state ($S_1$) is permitted to undergo fluorescence to a ground state ($S_0$) to produce the emission wavelength, the emission wavelength corresponding to the first singlet energy gap ($S_0$ to $S_1$); and
   imaging the biological tissue using the emission wavelength of 685 nm to produce an image of the biological tissue.

20. The method as recited in claim 19, further comprising a step of passing the emission wavelength through a filter that is selective for the emission wavelength, the step of passing occurring prior to the step of imaging.

21. The method as recited in claim 19, wherein the biological tissue is in vivo.

22. The method as recited in claim 19, wherein the step of providing indocyanine green (ICG) comprises a step of introducing the ICG into a blood vessel of a biological organism.

* * * * *